United States Patent [19]

Sethofer et al.

[11] 4,414,131
[45] Nov. 8, 1983

[54] GUEST-HOST LIQUID CRYSTALLINE COMPOSITION

[75] Inventors: Nicholas L. Sethofer; Michael C. Harper, both of San Jose, Calif.

[73] Assignee: Timex Corporation, Waterbury, Conn.

[21] Appl. No.: 457,781

[22] Filed: Jan. 13, 1983

Related U.S. Application Data

[63] Continuation of Ser. No. 319,349, Dec. 9, 1981, abandoned.

[51] Int. Cl.$^3$ .......................... G02F 1/13; C09K 3/34
[52] U.S. Cl. ............................ 252/299.1; 252/299.61; 350/349; 350/350 R; 549/369; 549/373; 549/375
[58] Field of Search ...................... 252/299.1, 299.61; 350/349, 350 R

[56] References Cited

U.S. PATENT DOCUMENTS

| | | | |
|---|---|---|---|
| 4,298,528 | 11/1981 | Sethofer | 252/299.61 |
| 4,323,471 | 4/1982 | Sethofer | 252/299.61 |
| 4,323,472 | 4/1982 | Sethofer | 252/299.61 |
| 4,324,455 | 4/1982 | Imahori et al. | 252/299.1 |
| 4,335,012 | 6/1982 | Sorkin | 252/299.61 |
| 4,344,856 | 8/1982 | Demus et al. | 252/299.61 |
| 4,348,324 | 9/1982 | Demus et al. | 252/299.61 |
| 4,356,104 | 10/1982 | Hsu | 252/299.61 |
| 4,364,838 | 12/1982 | Boller et al. | 252/299.61 |

FOREIGN PATENT DOCUMENTS 2067586 7/1981 United Kingdom ........... 252/299.61

OTHER PUBLICATIONS

Sorkin, H., Mol. Cryst. Liq. Cryst., vol. 56 (Letters), pp. 279–281 (1980).

*Primary Examiner*—Teddy S. Gron
*Attorney, Agent, or Firm*—William C. Crutcher; Joseph A. Biela

[57] ABSTRACT

A novel nematic liquid crystalline composition is provided. A novel liquid crystalline chiral compound, (+)5-(2-methyl) butyl-2(4-cyanophenyl)-1, 3-dioxane, is also provided. When admixed together, these novel components form a phase-change cholesteric liquid crystalline composition which is highly useful as the host medium in a guest-host electrooptical display as a result of its low electrical threshold and optical saturation voltages, steep saturation curve, relatively low optical birefringence, low viscosity and broad liquid crystalline mesomorphic range.

The host medium in conjunction with a suitable pleochroic dye provides an improved guest-host composition which exhibits a contrast of greater than 3:1 in certain displays, especially those having liquid crystal alignment layer means providing a moderate tilt angle of 10°–40° at the substrate/guest-host composition interface.

5 Claims, 6 Drawing Figures

GUEST-HOST LIQUID CRYSTALLINE COMPOSITION

This application is a continuation of application Ser. No. 319,349, filed Dec. 9, 1981, now abandoned.

FIELD OF THE INVENTION

This invention relates to improved electrooptical displays especially of the guest-host type and to liquid crystalline admixtures and to chiral additives useful as host media in such displays for providing improved contrast at low applied voltage in the multiplexed mode.

BACKGROUND OF THE INVENTION

The family of electrooptical display devices known generally as guest-host devices have high potential utility for information display purposes such as digital watches or clocks, calculators and other instruments. The typical guest-host device includes a pair of flat, parallel transparent substrates carrying transparent electrode segments on their facing surfaces and a mixture of nematic liquid crystal host compounds and a guest dichroic dye compound sealed between the substrates and electrodes. In this arrangement, the guest dye molecules tend to assume the orientation of the host liquid crystal molecules relative to the spaced substrates. The construction and operation of such guest-host electooptical display devices are well known as shown in the Helmeier U.S. Pat. No. 3,551,026 issued Dec. 29, 1970; the Ushiyama U.S. Pat. No. 4,241,339 issued Dec. 27, 1980; the Suzuki et al. U.S. Pat. No. 4,257,682 issued Mar. 24, 1981; and the Togashi U.S. Pat. No. 4,266,859 issued May 12, 1981.

In one type of guest-host display, the host liquid crystal molecules and therefore the guest dye molecules are aligned with their long axis parallel (homogenous) to the spaced substrates in the unactivated (off) state. However, when an electric field is generated across the electrode segment, the liquid crystal molecules align perpendicular (homeotropically) to the substrates as do the guest dye molecules. Since the dichroic dye molecules absorb only light whose electric vector lies along the long dye axis, the homeotropically aligned dye molecules absorb little light and the liquid crystaldye mixture between activated electrode segments appears essentially colorless or transparent to the viewer of incident light. Of course, homogenously aligned areas of the mixture appear colored or dark as a result of the perpendicular orientation of the dye molecules to the incident light. A display having light or colorless digits or symbols on a dark or color background is thereby provided.

However, guest-host display devices of this type suffer from a serious drawback in that, at best, the homogenously aligned dye molecules will absorb only 50% of the light incident upon the device, thereby resulting in poor display contrast. This limitation is due to the fact that only one polarization direction of the incident light has its electric vector aligned along the long axis of the dye molecule while the other polarization direction has its electric vector aligned transverse to the long dye axis. One attempted solution to this drawback has been to use well-known substrate surface alignment techniques such as rubbing to induce a 90° twist (helix) in the long axis of the homogenously aligned liquid crystal molecules from one substrate to the other much as in the well known twisted nematic liquid crystal electrooptical display devices, for example, see the Taylor and White U.S. Pat. No. 3,833,287 issued Sept. 3, 1974 and Coates and Gray U.S. Pat. No. 4,145,114 issued Mar. 20, 1979. The purpose of this helical molecular structure is to ensure that no matter what the orientation of the electric vector of the incident light, there will be a dye molecule at some distance between the spaced substrates with its long axis parallel to the vector to effect absorption. Thus, absorption of 90% or more of the incident light can be effected. Unfortunately, however, as is well known in conventional twisted nematic liquid crystal devices, the host liquid crystal exhibits a positive birefringence and tends to act as an optical waveguide so that the polarization of light transmitted through the device is twisted. Guest-host displays made with positive birefringent liquid crystal compounds are optically equivalent to a non-twisted homogenously aligned guest-host device with the attendant poor contrast.

The possibility of utilizing a host liquid crystal or mixtures thereof with minimal birefringent properties in such twisted guesthost display devices in order to increase contrast was initially proposed by Taylor in the *Journal of Applied Physics* 45(11), November 1974 at page 4,721. However, a practical mixture of liquid crystal compounds with low enough birefringence has not up to the present time been known or developed by prior art workers. The cyclohexyl-cyclohexane compounds first synthesized by Eidenschink et al., *Angew. Chem.* 133, p. 90 (1978) probably have low enough birefringent properties for twisted guest-host displays but mixtures containing these compounds are generally smectic rather than nematic at room temperature and also have low dielectric anisotropy which results in unacceptable slow response times during display operation and/or higher operating voltage. The phenyl cyclohexanes disclosed in the Eidenschink et al. U.S. Pat. No. 4,130,502 issued December 1978 require higher voltage levels and provide lower contrast which are not satisfactory for multiplexed electrooptical displays.

A copending patent application U.S. Ser. No. 136,855 filed Apr. 3, 1980, now U.S. Pat. No. 4,322,354, in the name of Howard Sorkin and of common assignee herewith discloses liquid crystal compounds of the formula:

where R is alkyl, alkoxy, aryl, aryloxy, carboxy or carboxy ester. These compounds have a very low electrical threshold voltage of approximately 0.6 volt, and relatively low optical birefringence of Δ n equal to 0.1 East German Pat. Nos. 139,852 and 139,867 disclose dioxane compounds of the general formula and liquid crystalline admixtures containing such compounds.

A copending patent application U.S. Ser. No. 135,381 filed Mar. 28, 1980, now U.S. Pat. No. 4,298,528, in the name of Nicholas Sethofer and of common assignee herewith describes liquid compounds of the formula:

when R and $R^1$ can be the same or different straight chain alkyl or alkoxy group. These compounds exhibit extremely low optical birefringence values of $\Delta n$ equal to 0.05 and in some cases 0.005. Liquid crystalline compounds having the formula:

where R and $R^1$ are as described are also disclosed in the referenced application as well as pending patent applications U.S. Ser. No. 219,672 filed Dec. 24, 1980, now U.S. Pat. No. 4,323,504, and U.S. Ser. No. 226,298 filed Jan. 19, 1981, now U.S. Pat. No. 4,323,473, and are useful in raising the clearing point of liquid crystalline compositions.

Also, a copending patent application U.S. Ser. No. 219,673 filed Dec. 24, 1980, now U.S. Pat. No. 4,325,830, in the name of Nicholas Sethofer and of common assignee herewith discloses three ring liquid crystalline compounds of the formula:

where $R_1$ is typically an alkyl group and $R_2$ is typically an alkyl, alkoxy, nitro or cyano group and ring N can be a benzene or cyclohexyl ring. These compounds are also useful in raising the clearing point of liquid crystalline compositions.

U.S. Pat. No. 4,200,580 issued Apr. 29, 1979 to Ying Yen Hsu and of common assignee herewith discloses compounds of the formula:

where $R_1$ is a straight chain alkyl of 1 to 10 carbon atoms and $R_2$ is alkyl, alkoxy, acyloxy, alkyl carbonato having 1 to 10 carbons, CN or $NO_2$.

A copending patent application U.S. Ser. No. 212,303 filed Dec. 3, 1980, now U.S. Pat. No. 4,313,878, in the name of the same inventor and also of common assignee herewith describes liquid crystalline compounds of the formula:

where $R_1$ and $R_2$ are as described in the U.S. Pat. No. 4,200,580.

Compounds of the 1,3 dioxane type having pharmaceutical use are disclosed in the Rhodes et al. U.S. Pat. No. 4,085,222 issued Apr. 18, 1978. These compounds, however, do not exhibit liquid crystalline behavior and are not useful in electrooptic displays.

Chiral or chiral containing additives for liquid crystalline compositions are also known. For example, the Coates et al. U.S. Pat. No. 4,195,916 issued Apr. 1, 1980 illustrates chiral esters and their use in electrooptic displays. The Gray et al. U.S. Pat. No. 4,219,256 issued Aug. 26, 1980 discloses compounds of the cyanophenylalkyl substituted bicyclo (2.2.2) octane type where the alkyl substituent may contain a chiral center. Three-ring compounds, in particular trans-4-alkylcyclohexane-1-carboxylic acid esters and ester derivatives of 1-carboxy4-alkyl substituted bicyclo (2.2.2) octane where the alkyl group may include a chiral center are taught in the Coates et al. U.S. Pat. No. 4,113,647 issued Sept. 12, 1978 and the Gray et al. U.S. Pat. No. 4,261,652 issued Apr. 14, 1981, respectively.

Commonly used chiral additives such as those of the cholesteryl nonanoate type produce a short helical molecular pitch in liquid crystalline mixtures but exhibit a weak dielectric anisotropy. Certain known optically active compounds such as 4-cyano-$4^1$- (2-methyl) butylbiphenyl (CB-15 available from BDH, Ltd.) produce only a moderate helical pitch and exhibit only moderate dielectric anisotropy which properties have not been adequate for low voltage, multiplexed operation.

What is still needed is a liquid crystalline host composition having substantially lower optical birefringence than currently available mixtures along with other required properties and improved chiral additives compatible with the host composition to provide a guest-host electrooptic display with improved contrast, e.g. a contrast ratio of 3:1 at voltages of about 3 volts.

SUMMARY OF THE INVENTION

One object of the invention is to provide a host liquid crystalline composition having low optical birefringence, low electrooptical threshold voltage, low saturation voltage and steep saturation curve.

Another object of the invention is to provide a novel chiral compound useful as an additive in liquid crystalline compositions, especially those provided herein.

Still another object of the invention is to provide a phasechange cholesteric guest-host liquid crystalline composition incorporating the novel chiral additive and one or more pleochroic dyes and exhibiting improved contrast such as at least a 3:1 contrast ratio in at least the biplexed mode of operation at voltages of 3 volts or below.

Still another object of the invention is to provide a guest-host electrooptical display device which includes constrast-enhancing alignment means.

The host liquid crystalline composition of the invention includes the following compounds with the specified formulas:

(I)

where $R_1$ and $R^1$ are alkyl especially straight chain, more especially $R_1$ is ethyl and $R^1$ is n-pentyl group, (II)

where $R_2$ and $R^1_2$ are alkyl, especially straight chain, more especially where $R_2$ is ethyl and $R^1_2$ is n-pentyl group.

(III)

where $R_3$ is alkyl, especially straight chain, more especially n-butyl, n-pentyl, n-hexyl and n-heptyl groups.

(IV)

where $R_4$ and $R^1_4$ are alkyl, especially straight chain, more especially where $R_4$ is n-propyl and $R^1_4$ is either n-pentyl or n-heptyl groups.

(V)

where $R_5$ is alkyl, especially straight chain, more especially either of n-propyl, n-butyl or n-pentyl groups.

Compounds I–V are present in the trans isomer configuration.

In a particular preferred embodiment of the host nematic liquid crystalline composition, compound I is present in an amount of 5 to 25 weight percent; compound II, 5 to 25 weight percent; compounds III total 40 to 80 weight percent, compounds IV total 10 to 40 weight percent and compounds V total 5 to 15 weight percent.

In a particular more preferred embodiment of the host liquid crystalline compositions, the compounds are present as follows:

|  | Weight % |
|---|---|
| 5-ethyl-2-(4-pentylcyclohexyl)-1,3-dioxane | 5–25 |
| 5-ethyl-2-[4-(pentylcyclohexyl)cyclohexyl]-1,3-dioxane | 5–25 |
| 5-butyl-2-(4-cyanophenyl)-1,3-dioxane | 10–30 |
| 5-pentyl-2-(4-cyanophenyl)-1,3-dioxane | 10–30 |
| 5-hexyl-2-(4-cyanophenyl)-1,3-dioxane | 10–30 |
| 5-heptyl-2(4-cyanophenyl)-1,3-dioxane | 10–30 |
| 5-propyl-2-[4-(4-pentylcyclohexyl)-phenyl]-1,3-dioxane | 5–25 |
| 5-propyl-2-[4-(4-heptylcyclohexyl)-phenyl]-1,3-dioxane | 5–25 |
| 4-cyanophenyl-4'-(5-propyl-1,3-dioxan-2-yl) | 1–5 |
| 4-cyanophenyl-4'-(5-butyl-1,3-dioxan-1-yl) | 1–5 |
| 4-cyanophenyl-4'-(5-pentyl-1,3-dioxan-2-yl) | 1–5 |

(VI)

where * represents an asymmetric carbon atom. This chiral compound is useful as an additive to liquid crystalline compositions, especially host liquid crystalline compositions described above, in additive amounts of about 1 to 10 weight percent.

The present invention also provides an improved phase-change cholesteric guest-host electrooptical composition as a result of including in the aforementioned host composition the chiral additive described above along with one or more pleochroic dyes.

The present invention also provides an improved guest-host electrooptical display device having contrast enhancing alignment means on the display substrate means, preferably in combination with the inventive cholesteric guest-host composition.

DESCRIPTION OF PREFERRED EMBODIMENTS

The compounds I through VI set forth hereinabove may be prepared as follows:

where R are alkyl chains, preferably straight chain with $C_2$ through $C_5$ and the optically active 2-methylbutyl isomer (in compound VI) and are:

Exact synthetic procedures for the types of compounds I through VI can be found in the following pending U.S. patent applications, the teachings of each of which are incorporated herein by reference:

Compound I—U.S. Ser. No. 135,381 filed Mar. 28, 1980, now U.S. Pat. No. 4,298,528.
Compound II—U.S. Ser. No. 219,672 filed Dec. 24, 1980, now U.S. Pat. No. 4,323,504, and Ser. No. 226,298 filed Jan. 19, 1981, now U.S. Pat. No. 4,323,473.
Compound III—U.S. Ser. No. 136,855 filed Apr. 3, 1980, now U.S. Pat. No. 4,322,354.
Compound IV—U.S. Ser. No. 219,673 filed Dec. 24, 1980, now U.S. Pat. No. 4,325,830.
Compound V—U.S. Ser. No. 212,303 filed Dec. 3, 1980, now U.S. Pat. No. 4,313,878.

An illustration of the preparation of the novel chiral compound is provided in the following Example:

EXAMPLE (+) 5-(2-methyl) butyl-2(4-cyanophenyl)-1,3-dioxane

(A)

where

The alkylation of a malonic acid ester was carried out with potassium carbonate in dimethyl formamide, reaction mixture being stirred for one week at room temperature to yield about 90% of compound II. Optically active (2-methyl)-butyl bromide was purchased from Aero Chemical Co., Newark, New Jersey. For full description of above synthetic step see U.S. Pat. No. 4,298,528 issued Nov. 3, 1981 to N. Sethofer. Reduction of alkyl malonic ester was carried out with lithium aluminum hydride in diethyl ether, by the method described in Fieser & Fieser: "Reagents for Organic Syntheses," Vol. 1, p. 584.

(B)

where

Final step in the (+) 5-(2-methyl) butyl-2-(4-cyanophenyl)-1-3-dioxane synthesis consists of condensation reaction, where aldehyde and 1.2 molar excess of optically active diol are refluxed with the catalytical amount of p-toluenesulfonic acid in benzene or toluene. Reaction is completed when calculated amount of water is collected in the attached Dean-Stark trap, e.g., on the average of 40 to 60 minutes. Reaction mixture is then cooled, washed first with 10% NaOH solution in water, then several times with water, layers separated and solvent evaporated.

Reaction yields mixture of trans and cis isomers of desired dioxanes, and on the average, about 5 to 10% of other impurities. The latter can be easily removed by crystalization from methanol. Separation of isomers (usually in 3:1 ratio for trans-cis in raw material) can be accomplished either by repeated crystalization from hexanes or by employing of chromatographic methods.

Compound IV, i.e., 4-cyanobenzaldehyde, was purchased from Aldrich Chemical Co., catalog No. C8-960-9.

The host liquid crystalline composition of the present invention is illustrated by means of the following example which is included for purposes of illustration rather than limitation:

EXAMPLE

| Structure | Weight % |
|---|---|
| $C_2H_5$-dioxane-cyclohexyl-$C_5H_{11}$ | 10.0 |
| $C_2H_5$-dioxane-cyclohexyl-cyclohexyl-$C_5H_{11}$ | 8.0 |
| $C_4H_9$-dioxane-phenyl-CN | 20.0 |
| $C_5H_{11}$-dioxane-phenyl-CN | 14.0 |
| $C_6H_{13}$-dioxane-phenyl-CN | 17.0 |
| $C_7H_{15}$-dioxane-phenyl-CN | 14.0 |
| $C_3H_7$-dioxane-phenyl-cyclohexyl-$C_5H_{11}$ | 8.0 |
| $C_3H_9$-dioxane-phenyl-cyclohexyl-$C_7H_{15}$ | 5.0 |
| $C_3H_7$-dioxane-phenyl-C(O)-O-phenyl-CN | 1.5 |
| $C_4H_9$-dioxane-phenyl-C(O)-O-phenyl-CN | 1.3 |
| $C_5H_{11}$-dioxane-phenyl-C(O)-O-phenyl-CN | 1.2 |

Typically, host liquid crystalline mixtures for multiplexable guesthost displays require the following characteristics, namely, low optical birefringence, extremely low electrooptical threshold and saturation voltage, broad temperature range and its own high order parameter in order to assure low voltage operation of the final guesthost complex in multiplexed displays. The admixture shown in Example I exhibits melting point of about $-20°$ C. (crystalline to nematic transition temperature), clearing point of 72.5° C. (nematic to isotropic transition temperature); $\Delta\eta$ of 0.097 (optical birefringence) at 22° C., viscosity about 30 cp at 25° C. The electrooptic characteristics of this admixture in a display with a 11 to 12 micron plate spacing and with 30°/12° SiO evaporation angle alignment layer (i.e. about 1°/20° molecular surface tilt angle) were as follows:

$V_{10}$(10% saturation)=0.95 V
$V_{90}$(90% saturation)=1.5 V
response time (ON)=90 ms
response time (OFF)=100 ms

Figure 1:
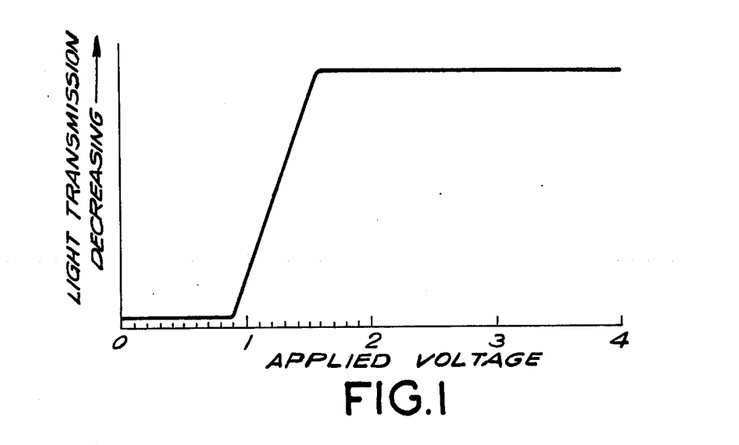
FIG. 1 is a graph of light transmission versus voltage for the exemplary nematic liquid crystalline composition of the Example I.

The above electrooptical data were obtained using known twisted nematic type cells, i.e. with 90° twist and 2 crossed polarizers. FIG. 1 is a representation of the electrooptical properties of the nematic admixture of Example I.

Preparation of the complexed guest-host mixture which is suitable for low voltage, multiplexed operation with contrast exceeding 3:1 ratio requires selection of a chiral additive which will have both an extremely large positive dielectric anisotropy and will produce a short molecular helical pitch when mixed with a nematic liquid crystal. The aforementioned commonly used chiral additives, such as cholesteryl momanoate (CHN) type or "optically active compounds" as 4-cyano- $4^1$(2-methyl)- butylbiphenyl(CB-15) have not proved satisfactory in meeting all of these characteristics, as mentioned already hereinabove.

Therefore, one of the objects of present invention is to provide an improved chiral addition for the hereinabove described mixture. Applicant have discovered that the compound (+)5-(2-methyl)butyl-2(4-cyanophenyl)-1,3-dioxane(OPDX) possesses the required charcteristics e.g. dielectric anisotropy ($\alpha\Sigma$) is greater than +17, melting point is 58.8° C., monotropic (1-CH)57.6° C.; $\alpha H = 5.0$ K CAL/MOLE, and cholesteric pitch of approximately one micron when present in an amount of 7 weight percent in the above described nematic composition (Example I).

Figure 2:
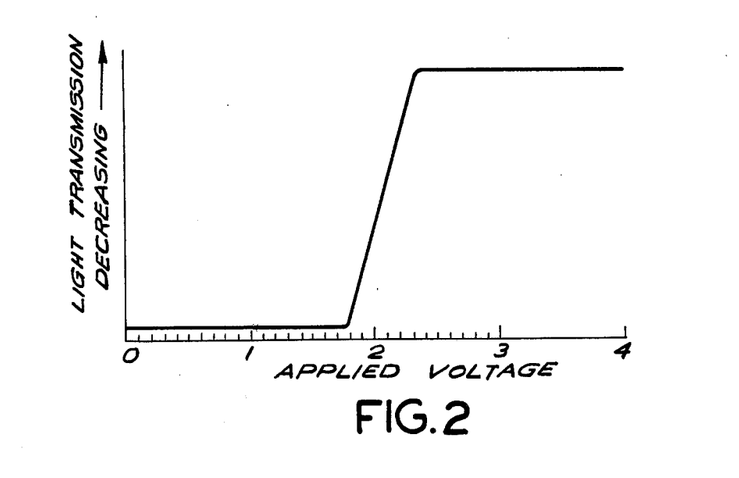
FIG. 2 is a similar graph for the cholesteric liquid crystalline composition obtained by adding 3 weight percent of the novel chiral additive to the composition of the Example I.

FIG. 2 is a plot of the electrooptical properties of a phasechange cholesteric-nematic liquid mixture obtained by introducing 3 weight percent of the above described chiral compound to the composition of Example I. This data were determined in a twisted nematic type display (90° twist) with a 11 to 12 micron plate spacing and with 30°/12° SiO evaporation angle alignment layer, i.e. a 1°/20° molecular surface tilt angle. Two crossed polarizers were used. FIG. 2 shows that under identical alignment conditions the electrical threshold was raised by 1 volt with 3% OPDX addition, while ratio $V_{SAT}$ and $V_{TH}$ remains virtually unchanged.

A guest-host electrooptical composition is provided by further introducing at least about 0.3 weight percent, preferably about 0.8 to about 1.2 weight percent of a pleochroic dye into the phase-change cholesteric nematic composition comprising Example I plus the novel chiral additive (i.e. 3 weight percent). Preferably, a pleochroic dye is used having an order parameter of greater than 0.7 as determined by conventional techniques. A preferred guesthost composition employs about 0.8 weight percent of the dye compound:

This dye compound is described more fully by Uchida et. al. in Mol. Cryst. Liq. Cryst., Vol. 34, (Lett.), pp. 150-158 (1977). Of course, those skilled in the art will appreciate that other known pleochroic dyes or mixtures of dyes can be employed.

Figure 3:
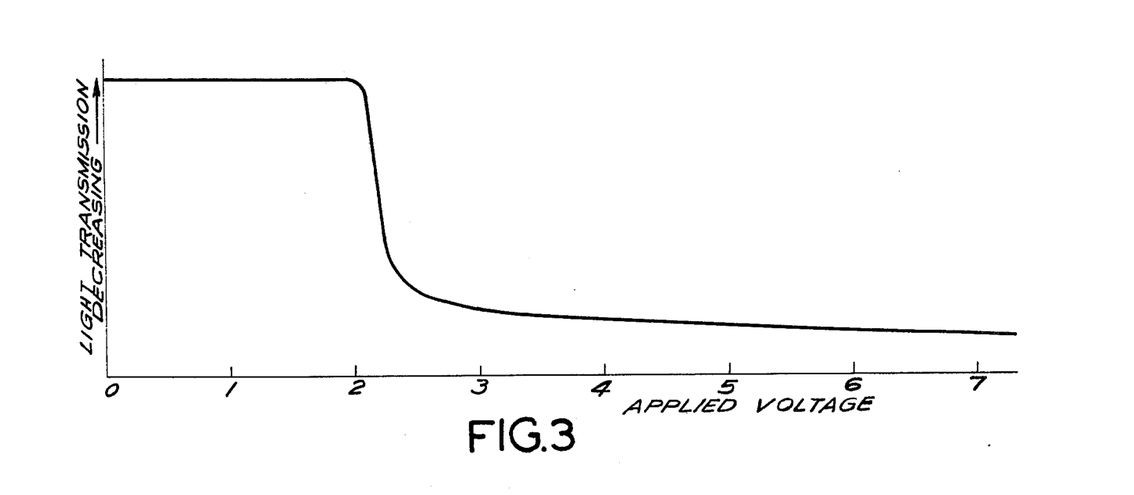
FIG. 3 is a similar graph for the cholesteric guest-host liquid crystalline composition obtained by adding 0.8 weight percent of pleochroic dye to the composition of FIG. 2.

FIG. 3 is a graph depicting the electrooptical properties of the preferred guest-host composition described above, i.e. Example I plus chiral additive (3 w/o) and dye (0.8 w/o). This data was generated using a display like that used to generate the electrooptical data of FIGS. 1 and 2 with the exception that no polarizers were used or required. Also, as in previous displays, the properties were measured in the transmission mode. The display exhibited light digits on a blue background with a contrast greater than 3 at a voltage of 3 volts. Some contrast increase beyond 3 volts can be attributed to homogeneous surface alignment; i.e. 30° SiO evaporation on one of the display plate surfaces.

Figure 4:
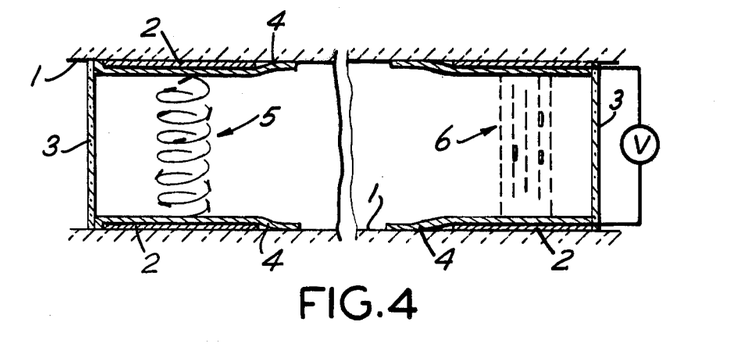
FIG. 4 is a schematic illustration of an electrooptical device of the guest-host type embodying features of the invention.

FIG. 4 is a schematic view of a basic structure of an electrooptical device of guest-host type according to the invention. The device can be driven in direct drive or multiplexed mode. Particular test device was driven in biplexed mode, respective rms voltages being 0.9 V and 2.4 VAC, frequency 32 Hz.

Figure 5:
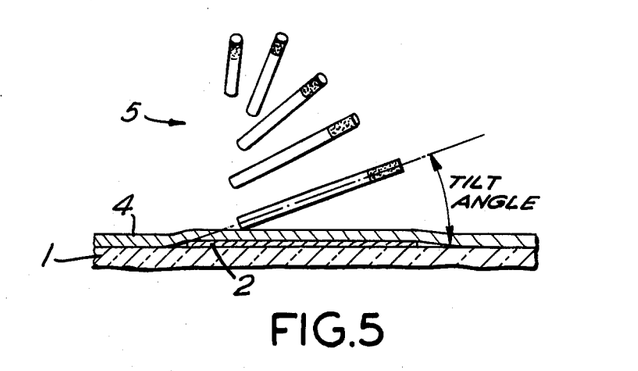
FIG. 5 is an enlarged view of FIG. 4 illustrating schematically the preferred tilt angle of the guest-host molecules to the display substrates.

The device consists of a cell with glass substrate 1 and spacer 3 (in this particular case 12 microns). Transparent electrodes 2 (typically indium oxide) and substrate 1 are covered with surface aligning SiO layer 4 which arranges the surface liquid crystal dye molecular layer so that a 10° to 40° tilt (measured relative to the substrate surface) is achieved (in this particular case tilt angle was 20° to 23°). FIG. 5 is an enlarged view showing the tilt angle of the molecules relative to the substrate.

Figure 6:
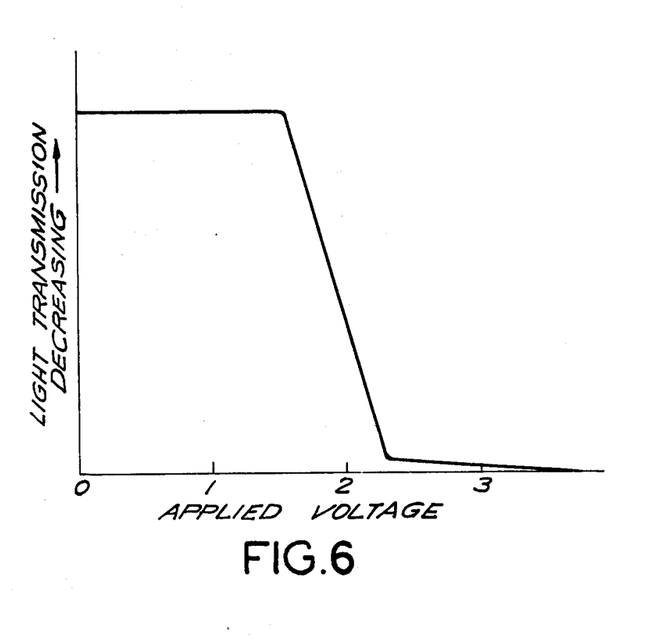
FIG. 6 is a graph of light transmission versus voltage for the display of FIG. 5 with the cholesteric guest-host composition of the invention.

The guest-host composition 5 (in this particular case the preferred mixture described above produces a helical structure in the off state, thus intensifying the color of the background by exposing more dye molecules for light absorption. The helix also controls the electrooptical threshold and steepness of the saturation curve (see FIG. 6) thus allowing the device to be multiplexed. Upon applying the required electric field between the electrodes 2, the cholesteric structure of layer 5 is disrupted and molecules align perpendicularly with their long axes to the substrate e.g. shown by reference numeral 6 in FIG. 4. Above described surface molecular pre-tilt of 20° to 23° assisted to a great extent in creating more complete homeotropic alignment under the electric field, thus diminishing coloration of energized segments and increasing the contrast of the device. Commonly used homogenous surface alignment (or rather low tilt angle up to 4°) of the prior art permits residula layers of liquid crystal and dye molecules to remain in the parallel direction to the glass substrate even after electrical field is applied, thus diminishing the contrast ratio at low voltages.

The electrooptical device of the invention can be employed in both transmissive and reflective modes. For the latter, Eastman White Reflectance coating (commercially available) was used as diffusing reflector. Other diffusing reflecting materials can be used by those skilled in the art.

I claim:

1. A guest/host nematic liquid crystalline composition having low optical birefringence and low threshold voltage comprising:
   (a) host nematic compounds: trans-alkyl pentylcyclohexyl dioxanes, trans-alkyl cyanophenyl dioxanes, trans-alkyl pentylcyclohexyl cyclohexyl dioxanes, trans-alkyl alkylcyclohexyl phenyl dioxanes and trans-cyanophenyl alkyl dioxanyl benzoates,
   (b) a chiral nematic compound having the formula:

(c) a guest pleochroic dye.

2. A guest/host nematic liquid crystalline composition having low optical birefringence and low threshold voltage comprising:
   (a) host nematic compounds in weight percent:

| | |
|---|---|
| trans $C_2H_5$—[dioxane]—H—$C_5H_{11}$ | 10.0 |
| trans $C_2H_5$—[dioxane]—H—H—$C_5H_{11}$ | 8.0 |
| trans $C_4H_9$—[dioxane]—O—CN | 20.0 |
| trans $C_5H_{11}$—[dioxane]—O—CN | 14.0 |

| | |
|---|---|
| trans C₆H₁₃—[dioxane]—[O]—CN | 17.0 |
| trans C₇H₁₅—[dioxane]—[O]—CN | 14.0 |
| trans C₃H₇—[dioxane]—[O]—[H]—C₅H₁₁ | 8.0 |
| trans C₃H₇—[dioxane]—[O]—[H]—C₇H₁₅ | 5.0 |
| trans C₃H₇—[dioxane]—[O]—CO—[O]—CN | 1.5 |
| trans C₄H₉—[dioxane]—[O]—CO—[O]—CN | 1.3 |
| trans C₅H₁₁—[dioxane]—[O]—CO—[O]—CN | 1.2 |

(b) a chiral nematic compound having the formula

CH₃CH₂*CH(CH₃)CH₂—[dioxane]—[Ph]—CN, and
(c) a guest pleochroic dye.

3. A guest/host nematic liquid crystalline composition having low optical birefringence and low threshold voltage comprising:
(a) host nematic compounds in weight percent:

| | |
|---|---|
| trans C₂H₅—[dioxane]—[H]—C₅H₁₁ | 5–25% |
| trans C₂H₅—[dioxane]—[H]—[H]—C₅H₁₁ | 5–25% |
| trans C₄H₉—[dioxane]—[O]—CN | 10–30% |
| trans C₅H₁₁—[dioxane]—[O]—CN | 10–30% |
| trans C₆H₁₃—[dioxane]—[O]—CN | 10–30% |
| trans C₇H₁₅—[dioxane]—[O]—CN | 10–30% |
| trans C₃H₇—[dioxane]—[O]—[H]—C₅H₁₁ | 5–25% |
| trans C₃H₇—[dioxane]—[O]—[H]—C₇H₁₅ | 5–25% |
| trans C₃H₇—[dioxane]—[O]—CO—[O]—CN | 1–5% |
| trans C₄H₉—[dioxane]—[O]—CO—[O]—CN | 1–5% |
| trans C₅H₁₁—[dioxane]—[O]—CO—[O]—CN | 1–5% |

(b) a chiral nematic compound having the formula

CH₃CH₂*CH(CH₃)CH₂—[dioxane]—[Ph]—CN, and
(c) a guest pleochroic dye.

4. The composition of claim 1 in which said trans-alkyl pentylcyclohexyl dioxanes is trans C₂H₅—[dioxane]—[H]—C₅H₁₁, said trans-alkyl cyanophenyl dioxanes are trans C₄H₉—[dioxane]—[Ph]—CN,

-continued said trans-alkyl pentylcyclohexyl cyclohexyl dioxanes is said trans-alkyl alkylcyclohexyl phenyl dioxanes are

-continued and said trans-cyanophenyl alkyl dioxanyl benzoates are

5. The composition of claim 1, 2, 3, or 4 in which said pleochroic dye has the formula:

* * * * *